(12) United States Patent
Ramirez et al.

(10) Patent No.: US 10,145,976 B2
(45) Date of Patent: Dec. 4, 2018

(54) ARRAYS OF RECEIVE ANTENNAS FOR MAGNETIC RESONANCE MEASUREMENTS

(71) Applicants: Marc S. Ramirez, Missouri City, TX (US); Carl M. Edwards, Katy, TX (US); Stanislav W. Forgang, Houston, TX (US); Babak Kouchmeshky, Kingwood, TX (US)

(72) Inventors: Marc S. Ramirez, Missouri City, TX (US); Carl M. Edwards, Katy, TX (US); Stanislav W. Forgang, Houston, TX (US); Babak Kouchmeshky, Kingwood, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 191 days.

(21) Appl. No.: 15/166,717

(22) Filed: May 27, 2016

(65) Prior Publication Data

US 2017/0343697 A1    Nov. 30, 2017

(51) Int. Cl.
  *G01R 33/383* (2006.01)
  *G01V 3/32* (2006.01)
  *G01R 33/34* (2006.01)
  *G01N 24/08* (2006.01)
  *G01R 33/3415* (2006.01)
  (Continued)

(52) U.S. Cl.
  CPC .............. *G01V 3/32* (2013.01); *G01N 24/081* (2013.01); *G01R 33/3415* (2013.01); *G01R 33/34046* (2013.01); *G01R 33/383* (2013.01); *G01R 33/3808* (2013.01); *G01R 33/365* (2013.01)

(58) Field of Classification Search
  CPC . G01V 3/32; G01R 33/3808; G01R 33/34046
  See application file for complete search history.

(56) References Cited

U.S. PATENT DOCUMENTS

| | | | |
|---|---|---|---|
| 4,825,162 | A  | 4/1989 | Roemer et al. |
| 6,720,765 | B2 | 4/2004 | Edwards et al. |
| 6,781,371 | B2 | 8/2004 | Taherian et al. |

(Continued)

OTHER PUBLICATIONS

Roemer, et al. "The NMR Phased Array" Magnetic Resonance in Medicine 16, 192-225 (1990).

*Primary Examiner* — Giovanni Astacio-Oquendo
*Assistant Examiner* — Alvaro Fortich
(74) *Attorney, Agent, or Firm* — Cantor Colburn LLP

(57) ABSTRACT

A nuclear magnetic resonance apparatus for estimating properties of an earth formation includes a carrier configured to be deployed in a borehole in the earth formation and at least one transmitting assembly disposed in the carrier and configured to generate an oscillating magnetic field in a volume of interest within the earth formation. The apparatus also includes at least one receiving assembly disposed in the carrier and configured to detect a nuclear magnetic resonance (NMR) signal originating in the volume of interest. In this apparatus, the receiving assembly includes at least a first longitudinal region with a loop coil and a butterfly coil, the loop coil central axis being located over a region of the magnet assembly where a static magnetic field is predominantly along an azimuthal direction to the carrier and the butterfly coil being at least partially overlapped with the loop coil to reduce mutual coupling.

23 Claims, 14 Drawing Sheets

(51) Int. Cl.
*G01R 33/38* (2006.01)
*G01R 33/36* (2006.01)

(56) References Cited

U.S. PATENT DOCUMENTS

| | | |
|---|---|---|
| 9,069,098 B2 | 6/2015 | Hopper et al. |
| 2004/0066194 A1* | 4/2004 | Slade ................. G01R 33/3808 324/318 |
| 2004/0183533 A1 | 9/2004 | Edwards et al. |
| 2012/0078558 A1* | 3/2012 | Pelegri ................... G01V 13/00 702/85 |
| 2013/0063142 A1 | 3/2013 | Hopper et al. |
| 2013/0093422 A1 | 4/2013 | Morys et al. |
| 2016/0131728 A1* | 5/2016 | Biber ................. G01R 33/3642 324/309 |

\* cited by examiner

ARRAYS OF RECEIVE ANTENNAS FOR MAGNETIC RESONANCE MEASUREMENTS

BACKGROUND

Understanding the characteristics of geologic formations and fluids located therein is important for effective hydrocarbon exploration and production. Formation evaluation relies on accurate petrophysical interpretation derived from a diverse set of logging technologies. One such technology, nuclear magnetic resonance (NMR), can be used to estimate formation characteristics such as mineralogy-independent porosity and permeability of rocks, to perform fluid typing and determine fluid volumes, and to estimate fluid characteristics such as viscosity. The design of NMR logging tools is crucial for achieving high performance, high measurement accuracy, and sufficient reliability in extreme high-temperature high-pressure environments. NMR-based tools can be conveyed into a borehole during drilling (e.g., logging-while-drilling) or after drilling (e.g., wireline logging).

SUMMARY

In one a nuclear magnetic resonance apparatus for estimating properties of an earth formation is disclosed. The apparatus includes a carrier configured to be deployed in a borehole in the earth formation and at least one transmitting assembly disposed in the carrier and configured to generate an oscillating magnetic field in a volume of interest within the earth formation. The apparatus also includes at least one receiving assembly disposed in the carrier and configured to detect a nuclear magnetic resonance (NMR) signal originating in the volume of interest. In this apparatus, the receiving assembly includes at least a first longitudinal region with a loop coil and a butterfly coil, the loop coil central axis being located over a region of the magnet assembly where a static magnetic field is predominantly along an azimuthal direction to the carrier and the butterfly coil being at least partially overlapped with the loop coil to reduce mutual coupling.

In another embodiment, a nuclear magnetic resonance apparatus for estimating properties of an earth formation that includes a carrier configured to be deployed in a borehole in the earth formation and at least one transmitting assembly disposed in the carrier and configured to generate an oscillating magnetic field in a volume of interest within the earth formation is disclosed. The apparatus also includes at least one receiving assembly disposed in the carrier and configured to detect a nuclear magnetic resonance (NMR) signal originating in the volume of interest. In this embodiment the receiving assembly includes at least a first region, a second region and a third region, each region offset longitudinally along the logging apparatus and including a loop coil having an additional outer loop and the additional outer loop of the loop coil of the first region overlaps the additional outer loop of the loop coil of the third region.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

FIG. 7A depicts static $B_0$ magnetic field patterns resulting from an exemplary magnet assembly, the fields at the front of the assembly are primarily along the azimuthal/circumferential direction to the tool and FIGS. 7B-7E depict the location and associated fields related to receive coils according to one embodiment;

FIG. 9A depicts static magnetic field patterns from an exemplary magnet assembly producing primarily radial static $B_0$ fields in the tool front facing the formation and FIG. 9B-9D depict the RF B1 fields related to the corresponding receive coils according to another embodiment. In particular, FIG. 9B shows a primary butterfly coil, FIG. 9C shows a rotated loop coil, and FIG. 9D shows an oppositely rotated loop coil;

DETAILED DESCRIPTION

Apparatuses and methods for measuring characteristics of an earth formation using magnetic resonance techniques are described herein. Embodiments of a nuclear magnetic resonance (NMR) apparatus or tool include an arrangement of transmit and receive antennas that may increase vertical resolution and/or depth of investigation. The NMR apparatus, in one embodiment, is a wireline or logging-while-drilling (LWD) device configured to take measurements at a series of depths or locations.

The arrangement of antennas may be such that receive antennas are arranged so that they are decoupled from one another. Such decoupling may be between adjacent (nearest neighboring coils) or non-adjacent neighbor coils, or both. Further, some embodiment may allow for the decoupling of overlaid transmit and receive antennas such that transmission and reception may be performed on distinct antennas.

In operation, a magnet assembly may include one or more distinct magnets (e.g., permanent magnets), with each magnet having a selected magnetic orientation. The magnet assembly forms a static magnetic field that is relatively strong at one side of the magnet assembly (e.g., the side directed toward the formation during measurements) and relatively weak or minimal at another (e.g., opposite) side of the magnet assembly (e.g., the side that is most proximal to the largest unoccupied portion of the borehole during measurements). The transmit and/or receive antennas may be aligned such that their fields are significantly orthogonal to one or more of the static fields produced by the magnets to improve sensitivity in the formation volume and/or aligned such that mutual inductance between antennas is reduced.

When deployed in a borehole and actuated to take NMR measurements of a formation, the magnet assembly generates a static external magnetic field that extends into a volume of interest in the formation, and that is weaker or minimal on the side adjacent to the unoccupied portion borehole. Embodiments described herein provide various benefits, such as improved measurement sensitivity.

Figure 1:
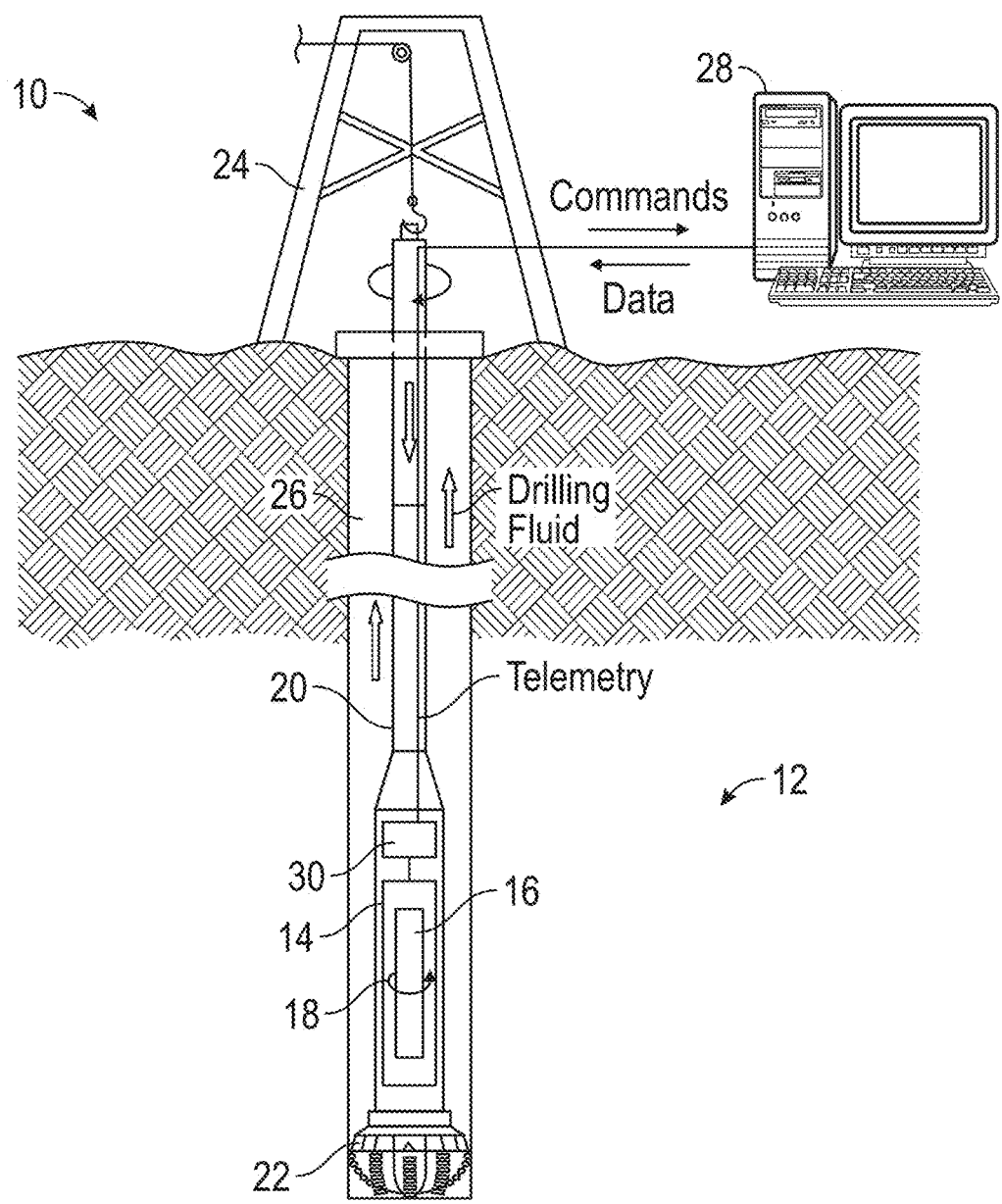
FIG. 1 depicts an embodiment of a formation measurement system that includes a nuclear magnetic resonance (NMR) measurement apparatus for logging while drilling.

FIG. 1 illustrates an exemplary embodiment of a downhole measurement, data acquisition, and/or analysis system 10 that includes devices or systems for in-situ measurement of characteristics of an earth formation 12. The system 10 includes a magnetic resonance apparatus such as a NMR tool 14. An example of the magnetic resonance apparatus is a logging-while-drilling (LWD) magnetic resonance tool. The tool 14 is configured to generate magnetic resonance data for use in estimating characteristics of a formation, such as porosity, irreducible water saturation, permeability, hydrocarbon content, and fluid viscosity.

An exemplary tool 14 includes a static magnetic field source 16 (e.g., the magnets described above) that magnetizes formation materials and a transmitter/receiver assembly 18 (e.g., an antenna, antenna array, or antenna assembly) that transmits RF energy or pulsed energy to provide an oscillating magnetic field in the formation. The assembly 18 may also serve the receive function, or distinct receiving antennas may be used for that purpose. It can be appreciated that the tool 14 may include a variety of components and configurations as known in the art of nuclear magnetic resonance or magnetic resonance imaging.

The tool 14 may be configured as a component of various subterranean systems, such as wireline well logging and LWD systems. For example, the tool 14 can be incorporated within a drill string 20 including a drill bit 22 or other suitable carrier and deployed downhole, e.g., from a drilling rig 24 into a borehole 26 during a drilling operation. The tool 14 is not limited to the embodiments described herein, and may be deployed in a carrier with alternative conveyance methods. A "carrier" as described herein means any device, device component, combination of devices, media and/or member that may be used to convey, house, support or otherwise facilitate the use of another device, device component, combination of devices, media, and/or member. Exemplary non-limiting carriers include drill strings of the coiled tube type, of the jointed pipe type, and any combination or portion thereof. Other carrier examples include casing pipes, wirelines, wireline sondes, slickline sondes, drop shots, downhole subs, bottom-hole assemblies, and drill strings.

In one embodiment, the tool 14 and/or other downhole components are equipped with transmission equipment to communicate ultimately to a surface processing unit 28. Such transmission equipment may take any desired form, and different transmission media and methods may be used, such as wired, fiber optic, and/or wireless transmission methods. Additional processing units may be deployed with the carrier. For example, a downhole electronics unit 30 includes various electronic components to facilitate receiving signals and collect data, transmitting data and commands, and/or processing data downhole. The surface processing unit 28, electronics 30, the tool 14, and/or other components of the system 10 include devices as necessary to provide for storing and/or processing data collected from the tool 14 and other components of the system 10. Exemplary devices include, without limitation, at least one processor, storage, memory, input devices, output devices, and the like.

In one embodiment, magnetic resonance measurements are performed by a nuclear magnetic resonance tool, which generates a static magnetic field ($B_0$) in a volume within the formation using one or more magnets (e.g., the magnetic field source 16). An oscillating (e.g., RF) magnetic field ($B_1$), which is at least substantially perpendicular to the static magnetic field, is generated in the volume with an RF antenna.

A receiving assembly detects the excited NMR signal and captures its relaxation back to thermal equilibrium. The signal originates from the net magnetization resulting from the superposition of signal from individual hydrogen protons in the formation fluid. These signals are formed using a series of spin echoes (i.e. resulting in an echo train), which are detected by the tool, numerically processed, and ultimately displayed in NMR logs. The amplitude of these spin echoes is detected as a function of time, allowing for detection of both the initial amplitude (i.e. for porosity measurement) and the signal decay, which can be used to derive other formation and fluid characteristics after the data inversion procedure.

When the magnetic moments of spin ½ nuclei, such as those of hydrogen nuclei, are exposed to a static magnetic field, they orient themselves at two angles (i.e. two energy levels) in respect to the static magnetic field and precess about the direction of the applied static magnetic field. At the relatively low static magnetic fields and high temperatures, typical for an NMR logging tool in an earth formation, the two energy levels have only slightly different populations, resulting in a very small net magnetization. Unfortunately the (static) net magnetization along the static magnetic field cannot be detected and requires the application of an RF field orthogonal to the static field to "tip" the net magnetization into the transverse plane where it precesses and generates a small alternating magnetic field that can be detected after application of rephasing pulses (also called refocusing pulses). The rate at which equilibrium is established in the net magnetization upon provision of a static magnetic field is characterized by the parameter T1, also referred to as the spin-lattice relaxation time constant. Another parameter is the spin-spin relaxation time constant, T2. Both, T1 and T2, are widely used to characterize the formation and the various fluids contained within the formation.

Figure 2A:
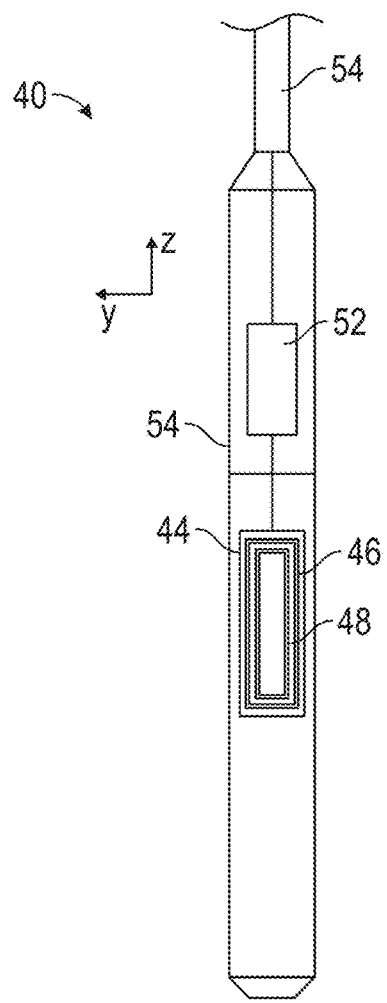
FIG. 2 depicts an embodiment of a NMR measurement apparatus for wireline logging.
Figure 2B:
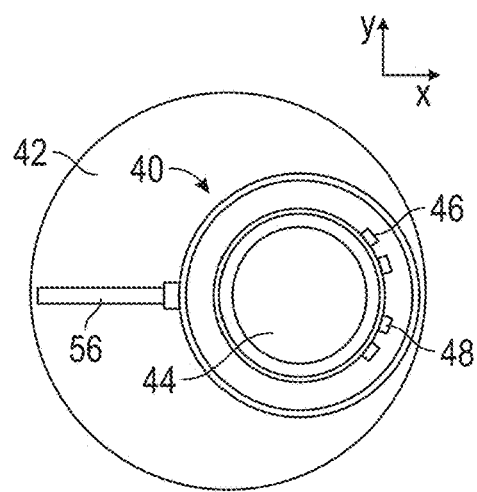

FIG. 2 illustrates an example of a measurement apparatus configured as a NMR tool 40 for logging a previously-drilled formation. The tool 40 in this example is configured as a wireline tool that may be deployed in an open borehole 42. The static magnetic field source includes one or more magnet assemblies 44. The magnet assemblies 44 described in embodiments herein are permanent magnets, but are not so limited. In one embodiment, the magnet assemblies include electromagnets, a combination of permanent magnets and electromagnets, or magnets in combination with soft magnetic materials. One or more transmit and/or receive antennas are disposed proximal to each permanent magnet assembly 44. In this example, the tool 40 includes a transmitter assembly that includes an antenna in the form of a transmitting loop coil 46 and a receiving antenna in the form of a receiving loop coil 48. The antenna configurations are not limited to those described herein. For example, the antennas may be wrapped circumferentially around the magnet assembly or have a different shape or orientation. In other examples, a single coil or group of coils can be configured as both a transmitting and receiving device.

Other components of the tool include, for example, a sonde 50 or other carrier, and an electronics unit 52 connected to the coils 46 and 48, and/or to the magnet assembly 44. The electronics unit 52 and/or coils are connected to a surface location via a wireline 54 or other suitable telemetry system.

In this example, the tool 40 is a directional tool placed against the borehole wall and configured to generate strong magnetic fields in a volume of interest within the formation. The magnet assembly 44 is oriented so that the static magnetic fields are generally in the transverse (i.e. x-y) plane perpendicular to the length of the borehole and the longitudinal tool axis (the z-axis in this example), and is oriented generally toward the volume of interest. The transmitting coil 46 in this example is oriented generally in a plane perpendicular to the x-axis and emits an oscillating magnetic field at least substantially along the x-axis. The receiving coil 48 is oriented in the same direction as the transmitting coil 46. The coils are "side-looking" in that they are oriented to emit a magnetic field in a specific angular region about the longitudinal borehole (z-directed) axis. Components such as an extendable arm 56 may be included and actuated to urge the emitting side of the tool 40 toward the borehole wall, to increase the field strength in the volume of interest, and to reduce or eliminate the influence of borehole fluids on the acquired signal.

Figure 3:
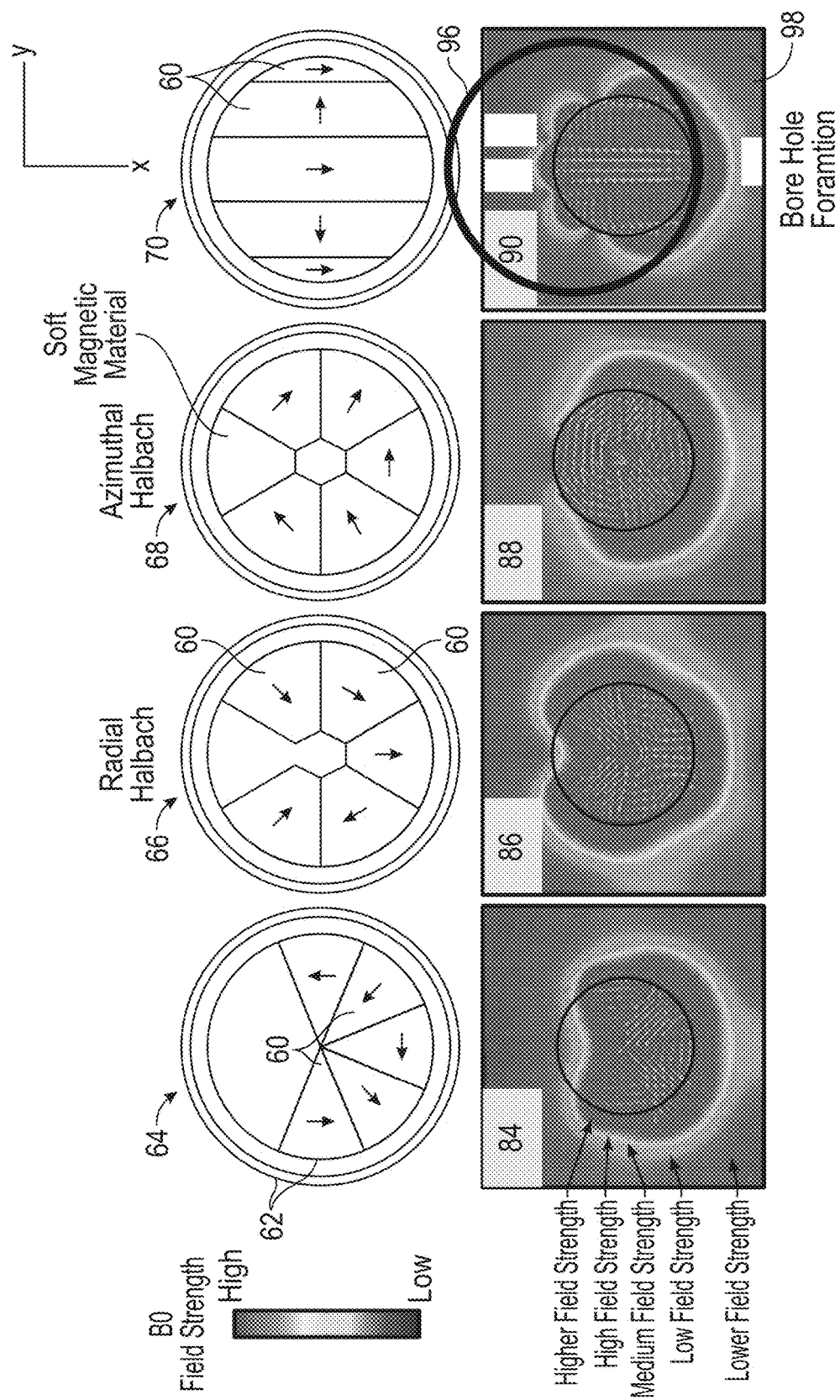
FIG. 3 depicts exemplary magnet assemblies configured to generate a static magnetic field for NMR measurements along with examples of their associated fields.

FIG. 3 illustrates various embodiments of magnet assemblies configured to generate a static magnetic field for magnetic resonance measurements. Each embodiment may be incorporated in a NMR measurement apparatus, e.g., as the magnet assembly 44, or in any other downhole magnetic resonance device or other device that involves generating a magnetic field in a formation or borehole. Each magnet assembly includes an arrangement of permanent magnets 60, electromagnets, or a combination of permanent and/or electromagnets and core sections made from soft magnetic materials. The array of magnets 60 are configured to generate a static external magnetic field, $B_0$ in the formation Each magnet assembly generates a pattern of magnetic field orientations that results in a relatively strong magnetic field on one side of the assembly (a primary side) and a relatively weak or minimal magnetic field on an opposite or adjacent side of the assembly. FIG. 3 shows a cross-section in an x-y plane perpendicular to the longitudinal axis (z-axis) of the measurement apparatus. The orientation of the magnetic fields in this plane is shown for each magnet by a collection of arrows. As one progresses along each adjacent magnet 60 in the array (either linearly or along a circumferential path), the angular direction or phase of each magnet segment changes according to a selected pattern. In one embodiment, the array has a rotating pattern of orientations similar to that of a Halbach array.

Exemplary patterns of the magnet array are shown in FIG. 3. The magnet geometries, magnetic orientations, and associated $B_0$ fields are shown for each example pattern. Although the assemblies shown here are cylindrical or semi-cylindrical, other shapes and cross-sections may be used. In one embodiment, as shown in FIG. 3, the magnets 60 in the array are placed in contact with one another and affixed to one another by any suitable means. In some examples, the magnets 60 form an array that is wrapped around a center of the assembly along a circumferential path that may be defined by the periphery 62 of the tool.

A first exemplary magnet assembly 64 includes an array of wedge or pie-shaped magnets 60 forming a full or partial cylinder. A second assembly 66 includes an array of magnets 60 arranged in a semi-circular pattern around an empty central portion, which can be used as a conduit for routing cables or fluid, or used to provide space for material that offers structural support. In this example, alternating magnets 60 in the assembly (i.e., every other magnet) have an orientation that is in the radial direction toward, away, or perpendicular to the center of assembly 66, and the overall $B_0$ field pattern exits the front of the tool (i.e. the part of the tool intended to make contact with the borehole) and returns primarily at two distinct locations at a given angular offset around the tool circumference.

A third assembly 68, referred to as an azimuthal assembly, also includes an array of wedge-shaped magnets (although pie or similar shapes could also be used) arranged in a semi-circular array around a non-magnetic central segment. Assembly 70, for instance, includes an array of magnets forming a solid cylinder, although similar configurations with soft magnetic materials, void spaces, and/or materials providing structural support can also be employed. The array of magnets 60 progresses linearly (e.g., along the y-axis), and the orientation of the magnets 60 in the array rotates as the magnets 60 progress from one end of the array to the other.

In each embodiment shown in FIG. 3, the magnet assembly is configured to generate a static magnetic field $B_0$ that is relatively strong and/or has a larger area on the side of the NMR measurement apparatus that is directed toward the volume of interest. In this way, the field can be applied to a region of the borehole wall and/or formation, while generating a smaller or minimal magnetic field strength adjacent to the primary field or directed toward the largest unoccupied portion of the borehole.

Figure 4A:
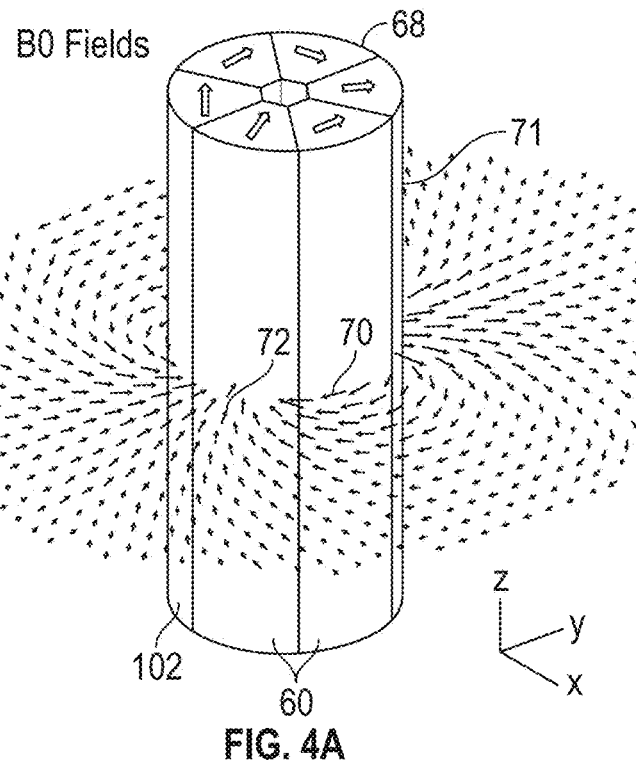
FIGS. 4A-4B depicts components of an embodiment of an NMR measurement apparatus, including a magnet assembly and a transmit/receive antenna assembly (e.g., a radiofrequency (RF) coil) configured to generate an oscillating magnetic field in the formation and to perform signal reception; Static ($B_0$) and RF ($B_1$) fields are shown for the magnet assembly and antenna respectively
Figure 4B:
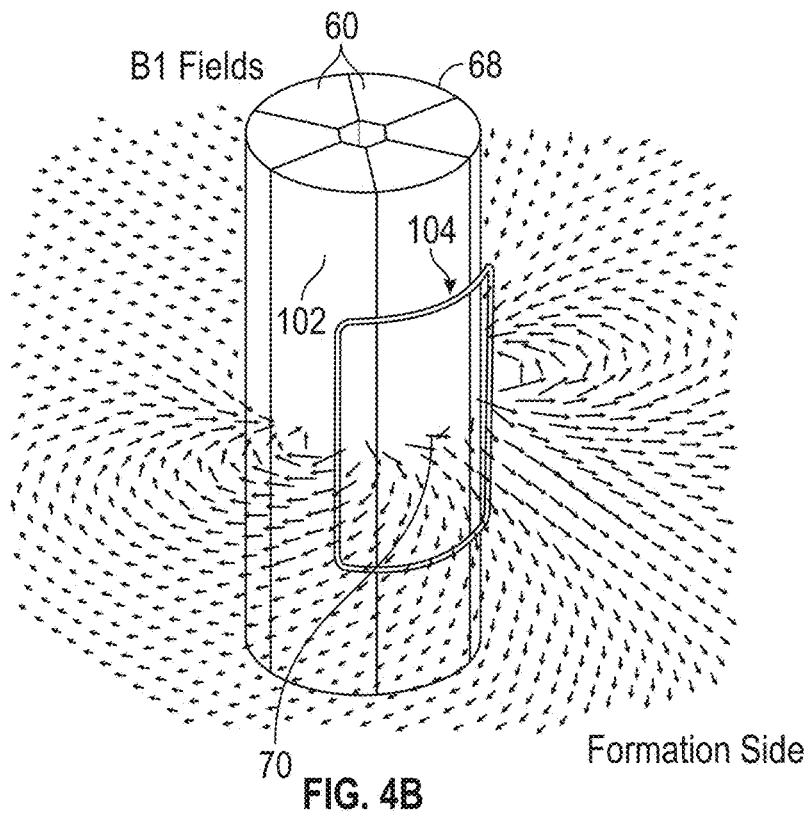

FIGS. 4A and 4B shows an embodiment of an NMR apparatus that includes a magnet assembly having an azimuthal static field orientation in front of the tool, i.e. facing the formation volume on interest, and in the x-y plane, with ideally no or minimal z-directed fields. The antenna assembly includes a loop coil 104 in FIG. 4B, which is positioned azimuthally so that the loop coil's interior magnetic field is directed toward a volume of interest within the formation. The magnetic fields $B_0$ of the magnet assembly have directions shown by arrows in FIG. 4A that are largely orthogonal to those produced by the RF antennas. The loop coil as shown is exemplary only and may include an additional outer loop portion as described below or may have a non-symmetric geometry.

The RF antenna assembly is configured to receive an oscillating magnetic field $B_1$ within a given frequency range. In one embodiment, the tool 100 includes an antenna configured as a loop coil 104 having a rectangular path and generally conforming to the exterior surface of the side of the magnet assembly (largely perpendicular to the x-y plane). The magnetic $B_1$ field of the loop coil is generally oriented in a radial direction along the central coil axis toward the formation. The directions of the $B_1$ fields are shown with arrow plots in FIG. 4B. That is, in one embodiment, the loop coil 104 is arranged to overlie the magnets such that the $B_1$ exits from the center of the loop coil, precisely where the static $B_0$ field is azimuthally (and orthogonally) directed as shown by reference numeral 70 in FIG. 4A. The location where the $B_0$ fields leaves the array 102 is shown by reference numeral 71 and the location where the $B_0$ fields enter the array 102 is shown by reference numeral 72.

Figure 5:
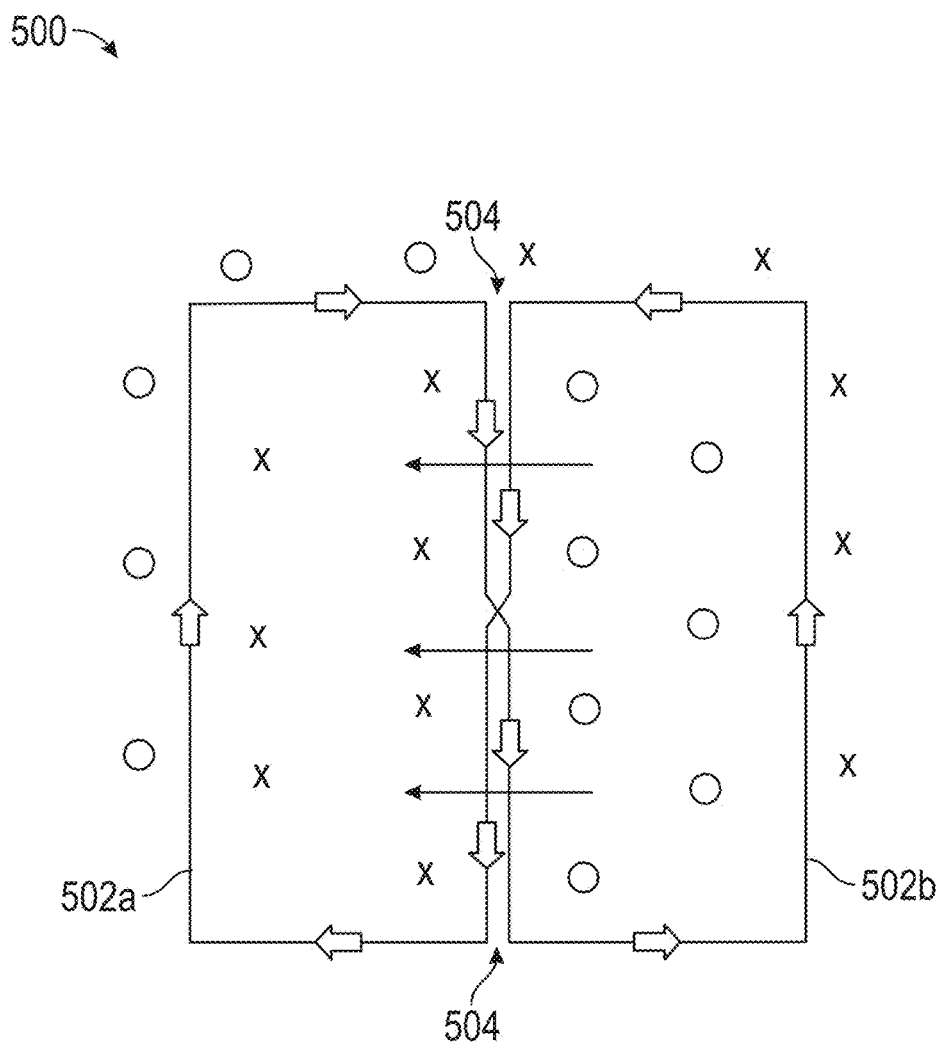
FIG. 5 shows an example of a butterfly coil. The coil consists of several conducting segments in series, with a possible current path and associated magnetic flux pattern displayed.

With reference now to FIG. 5, an alternative form of a receive coil 500 is shown. This type of receive antenna shall be referred to as a butterfly coil and includes first and second coils or loops 502a, 502b connected by a cross-member 504. Overall, the coil segments form a continuous path that produces a distinct $B_1$ pattern, as shown in FIG. 5. "o" symbols represent magnetic flux directed out of the page and "x" symbols represent magnet flux directed into the page. At the crossover point, magnetic flux is directed horizontally from one loop to the other as indicated by the long arrows.

Figure 6:
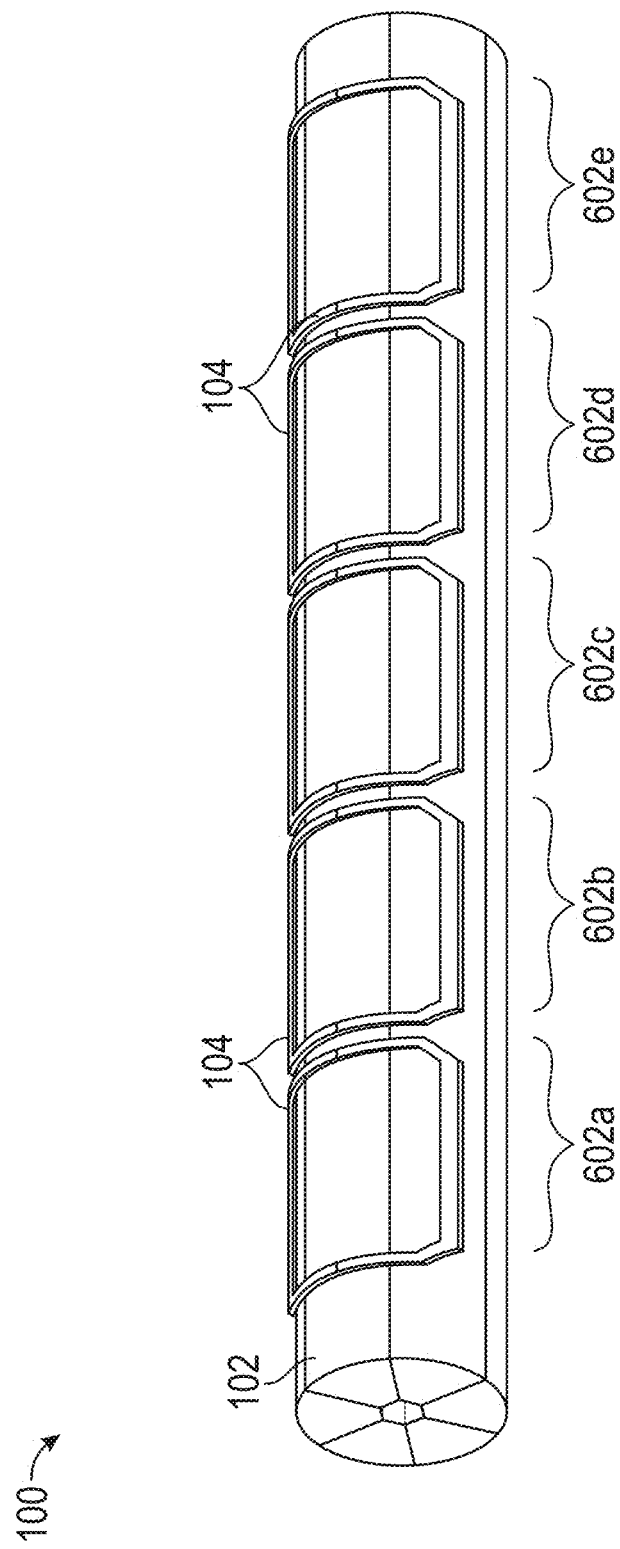
FIG. 6 depicts components of an embodiment of an NMR measurement apparatus that includes an array of antennas for reception, in combination with a magnet assembly for generating a static $B_0$ field in the formation.

In one embodiment, the antenna includes a combination of one or more loop coils extended along the length of the magnet assembly 102 (i.e. the longitudinal direction). FIG. 6 shows an exemplary configuration of a NMR apparatus including a permanent magnet array and a RF antenna assembly used to extend sensitivity. As shown, each loop cool 104 is a receive coil and FIG. 6 is presented to generally illustrate that each loop coil 104 defines a particular region 602a-602e. As shown, the loop coils are separate from each other but, as discussed below, in at least one embodiment, the loop coils will overlap one another. Further, it shall be understood that the magnet assembly 102 can be any of the arrays 102 described above or any magnet configuration that generates similar static fields.

Figure 7A:
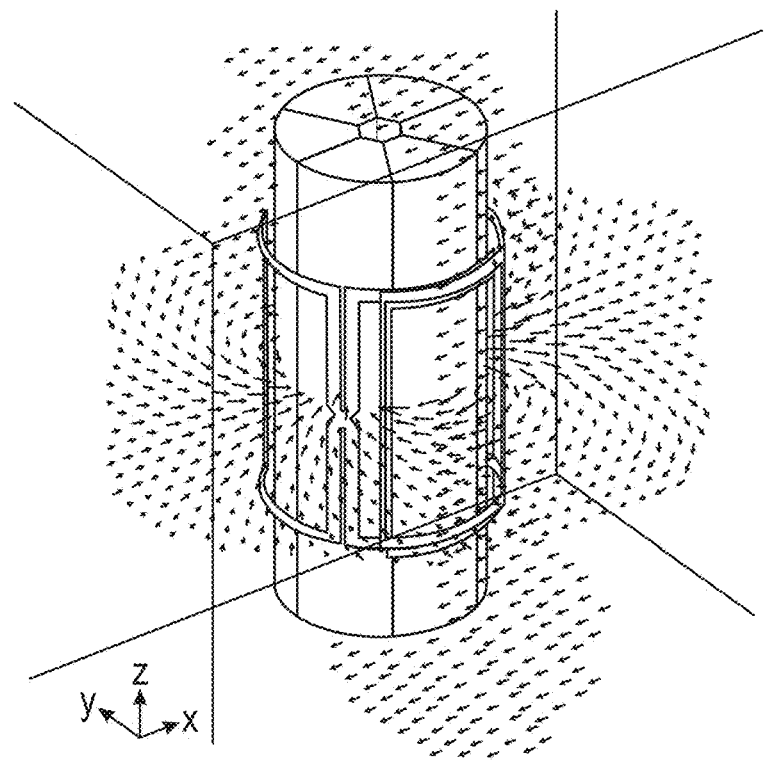
FIGS. 7A-7E show fields associated with magnets and coils of one embodiment. In particular.
Figure 7B:
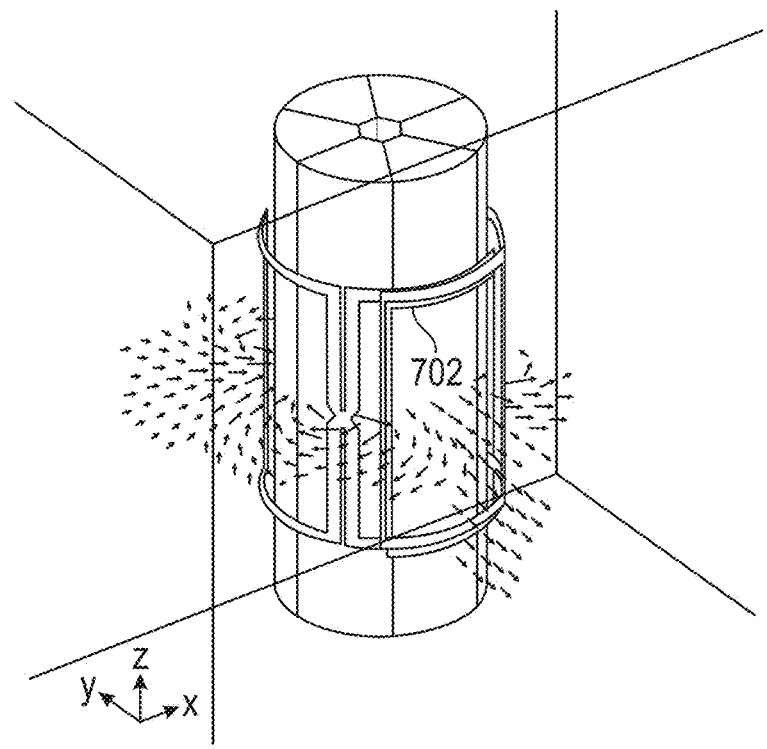
Figure 7C:
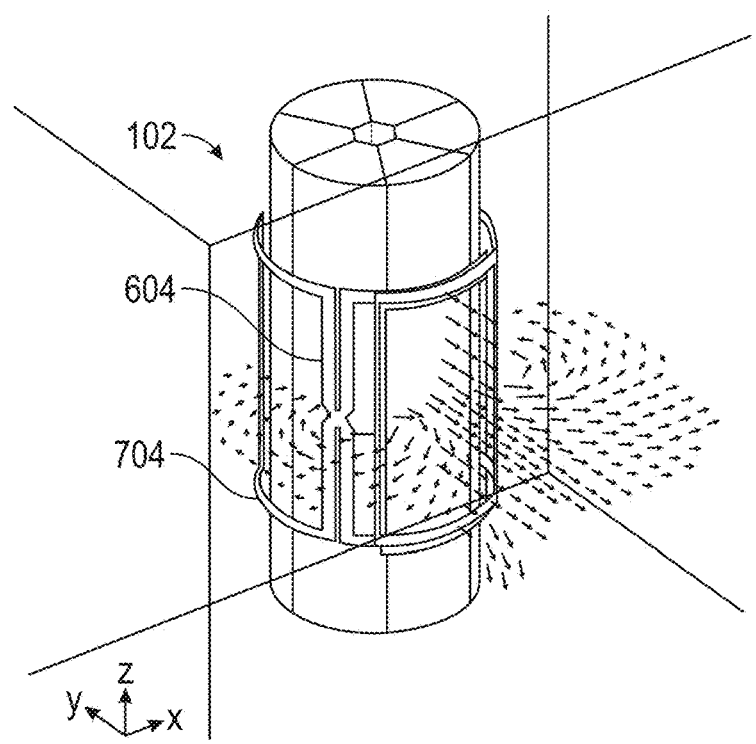
Figure 7D:
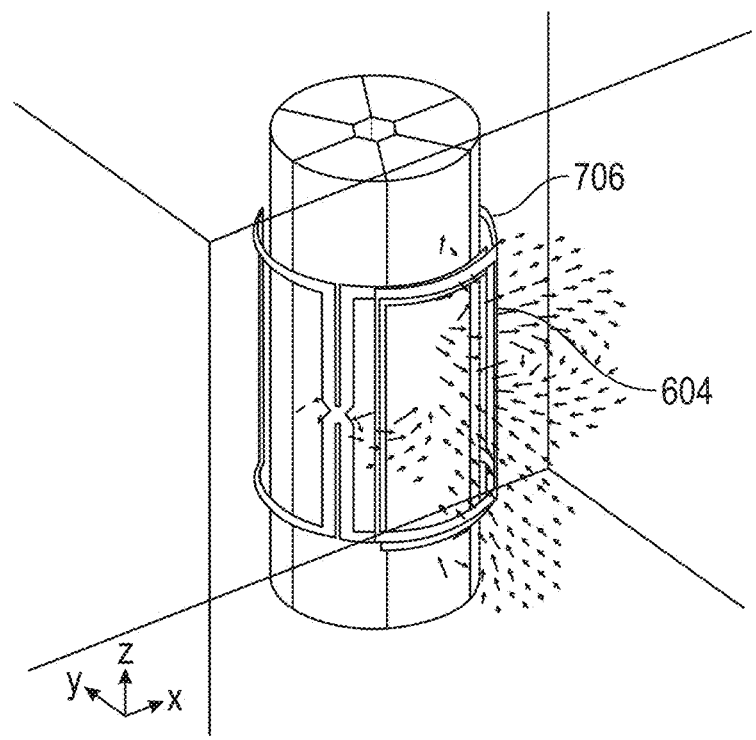

In one embodiment, the magnet assembly 102 is an azimuthal Halbach arrangement (e.g., FIG. 3). In that embodiment, and with reference now to FIG. 7A, the magnet assembly 102 produces a specific $B_0$ field pattern. In FIG. 7B-7D, the spatial distribution of $B_1$ fields is substantially orthogonal to the corresponding $B_0$ field pattern shown in FIG. 7A.

A first loop coil 802 is arranged such that its $B_1$ is directed primarily from roughly the center of the first loop coil out toward the formation volume of interest 702. Two butterfly coils 804 and 806 are arranged such that the cross members 604 of each are located at the locations of magnetic flux exiting from and returning to the magnet assembly. That is, the cross members are arranged such that their corresponding $B_1$ fields (as illustrated in FIG. 5) at the crossover location are substantially perpendicular to the static magnetic fields of the magnet assembly. In other words, the crossover locations are placed at the exit and return flux locations of the magnets (e.g., where the $B_0$ fields leave and return to the magnet 102) and the loop coil is over the magnet center where the $B_0$ fields are pointing azimuthally about the magnet 102. Thus, as shown in FIGS. 7B-7D, each longitudinal region of an antenna array 602 can include at least one loop coil 702 and two butterfly coils 704, 706 arranged as described above.

Figure 8A:
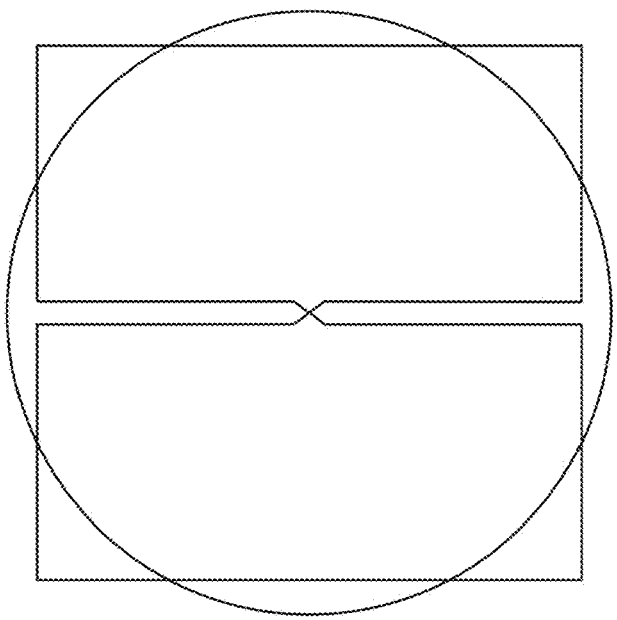
FIGS. 8A and 8B show two-element stacked antenna orientations containing a primary loop coil and a butterfly coil (8A), along with two butterfly coils with orthogonal cross-members (8B), each of which results in high levels of mutual inductive decoupling between one another by segment geometry (i.e. symmetry) and the associated magnetic flux patterns.
Figure 8B:
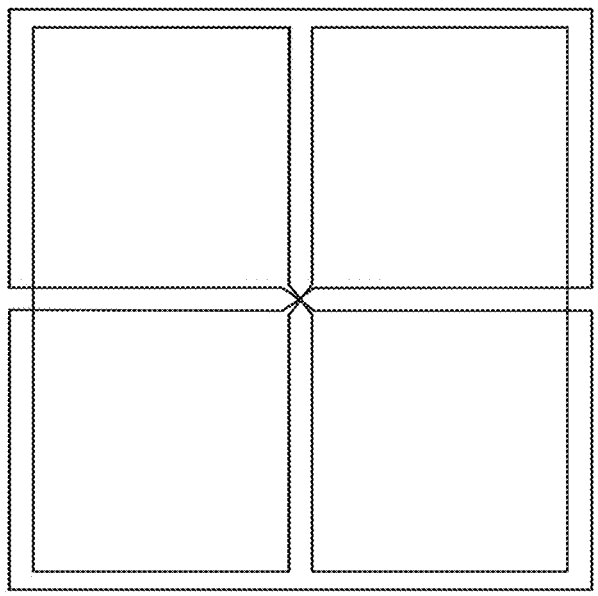
Figure 9A:
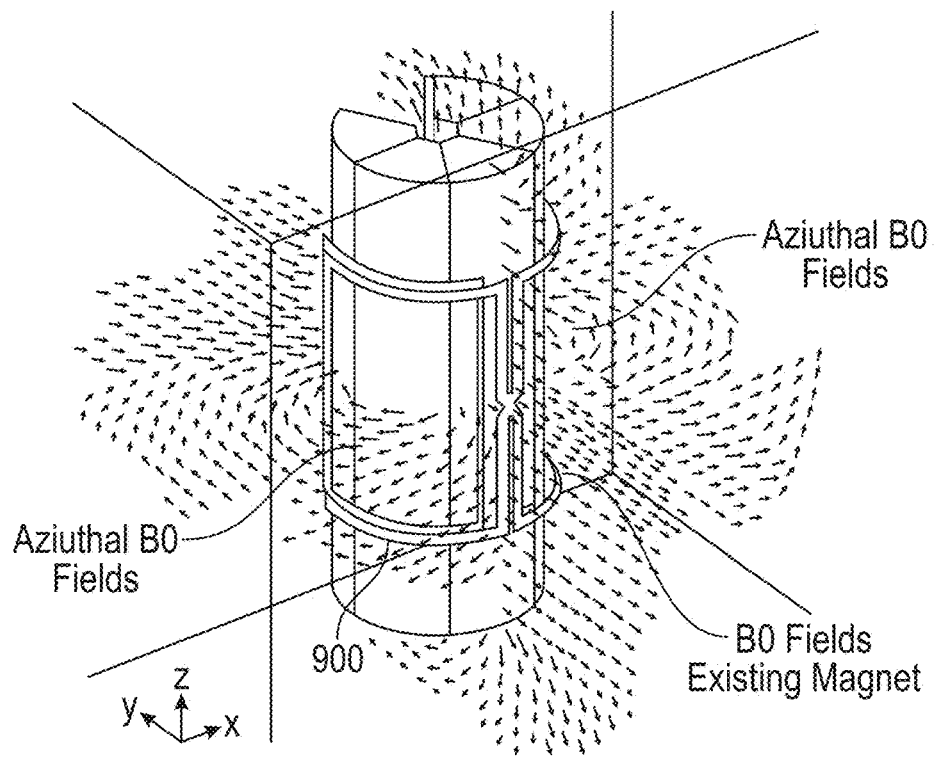
FIGS. 9A-9D depict various magnetic fields of one embodiment. In particular.
Figure 9B:
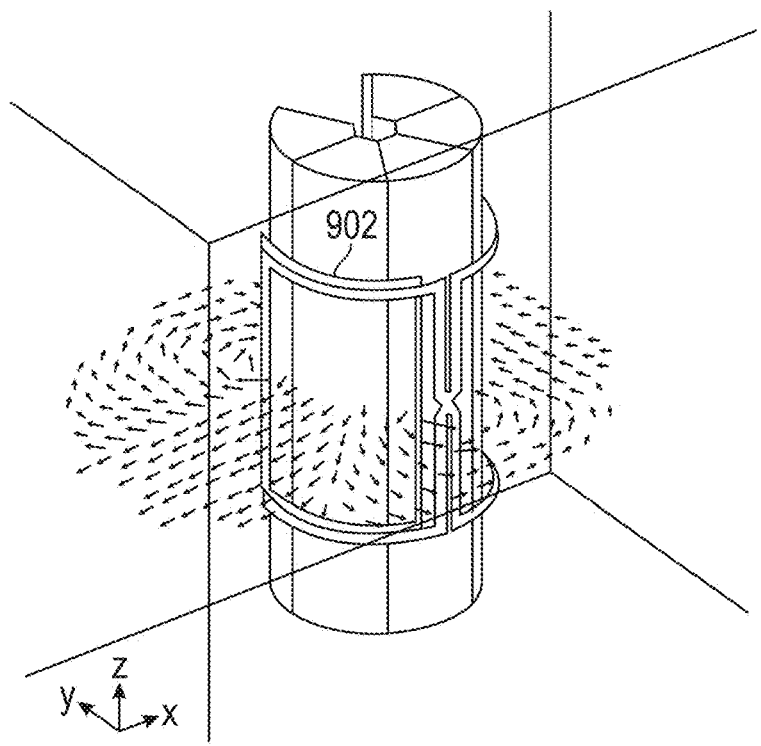
Figure 9C:
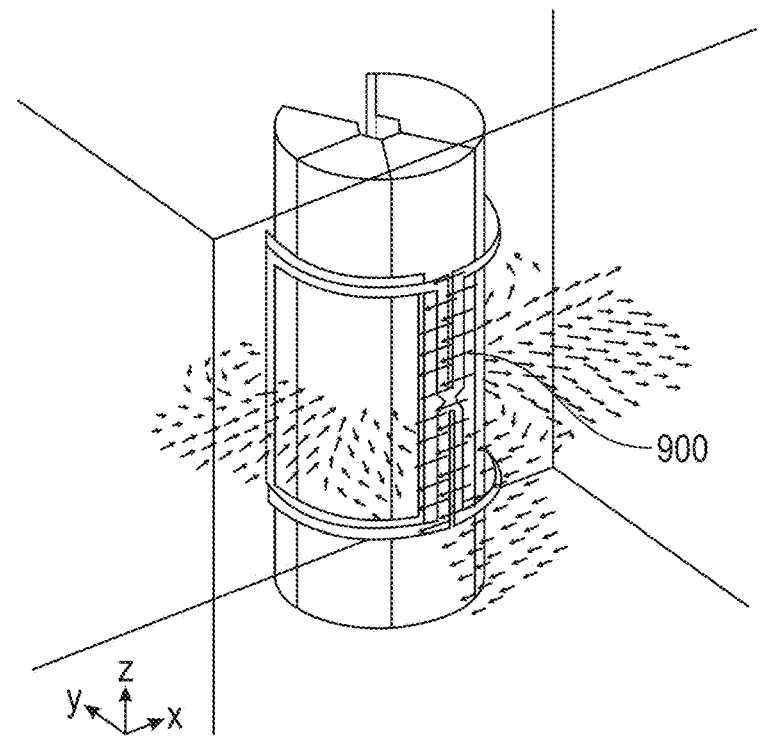
Figure 9D:
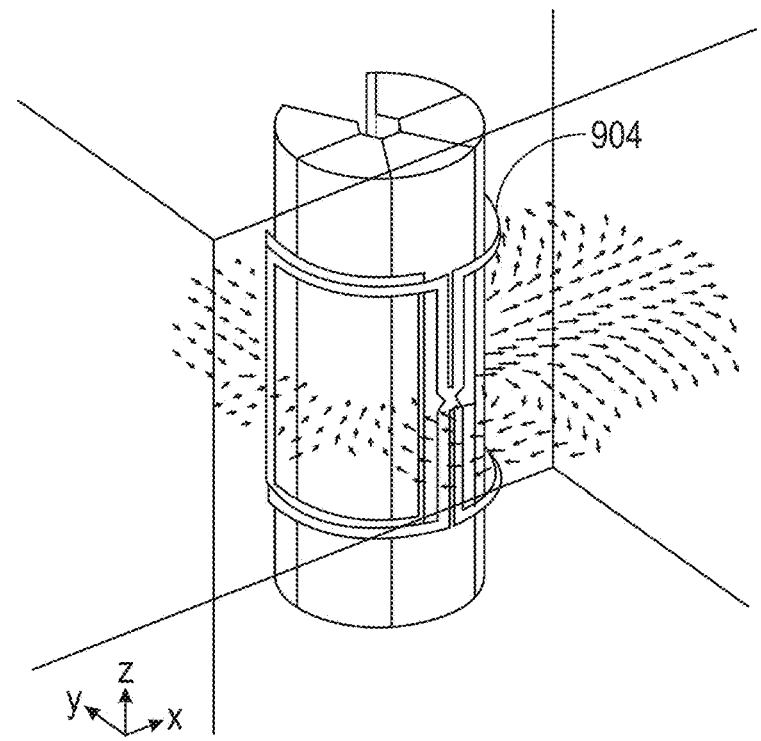

The above description has focused on the location of the loop and butterfly coils in relation to the $B_0$ fields. Based on this description, it shall be understood that the locations may be defined based on minimizing mutual inductance (i.e. coupling) among receive coils. The butterfly coils may be precisely aligned, either by rotation of the coil or by varying the dimension of the overlapping loop such that mutual inductance is canceled and coupling is minimized. By symmetry illustrated in FIG. 5, butterfly coils can be positioned such that their central axis is equal to the central axis of a surrounding or overlapping loop coil or with a common central axis to another symmetric butterfly coil rotated by 90 degrees i.e. with cross-members orthogonal to each other. These properties allow coils to be completely overlapped or surrounded and still maintain the properties of minimal mutual coupling. FIGS. 8A-8B indicates such two-element geometries.

Figure 7E:
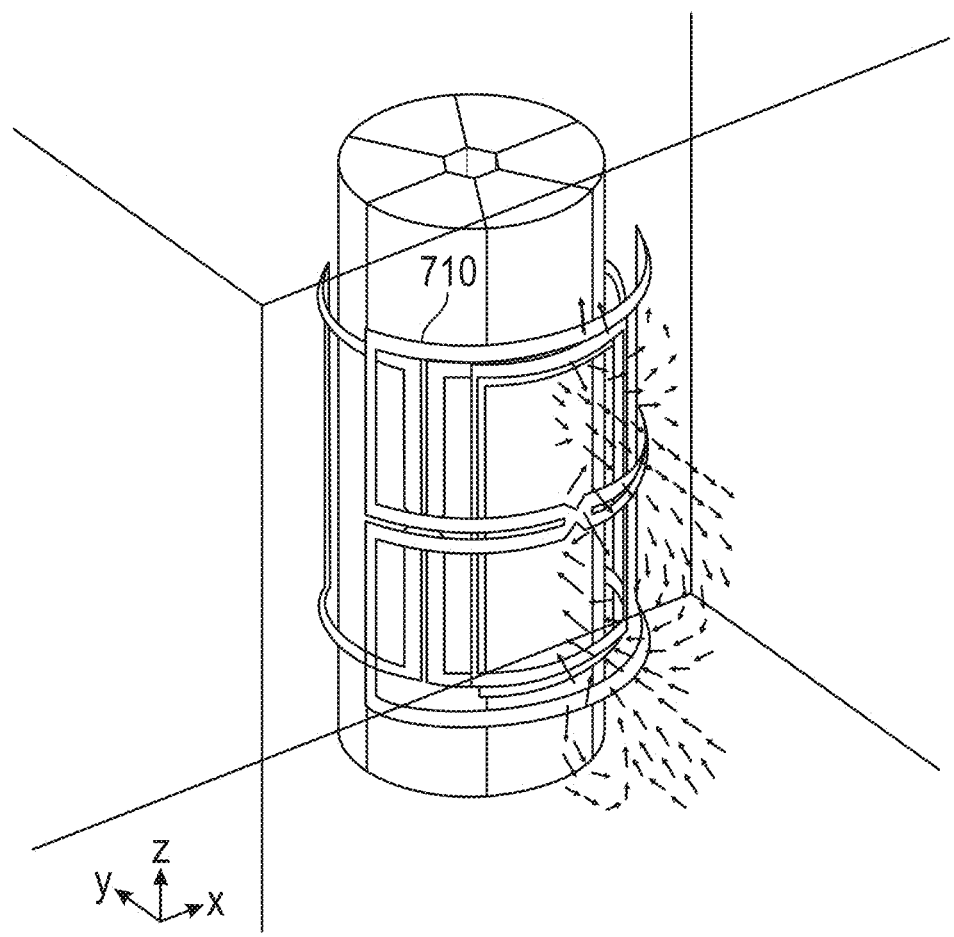

Based on this principle, and referring to FIG. 7E, it shall be further understood that a third butterfly coil 710 may be arranged such that its cross member is largely perpendicular to those of first and second butterfly coils 704, 706 and such that its $B_1$ fields are orthogonal to the static $B_0$ fields, since the static fields are primarily maintained in the transverse x-y plane.

An alternative embodiment is shown in FIGS. 9A-9D, which is complementary to that previously described. Here, one butterfly coil (900) is optimally placed in the magnet front, where B0 fields point radially out toward the formation. Two loop coils (902, 904) are rotated at a particular angle (in opposite directions) to maximize orthogonality with the static B0 fields, which are in the azimuthal direction at the coil centers. Also similarly, a third butterfly coil may be added to this configuration if it is rotated by 90-degrees, as demonstrated in FIG. 7E and as illustrated in FIG. 8B As discussed above, each region 602 can include from one loop coil and up to 3 butterfly coils in one embodiment as described above, or up to 2 loop coils and 2 butterfly coils in the second embodiment (FIGS. 9A-9D). In one embodiment the primary loop coils overlap one another along the longitudinal direction. It has been discovered that arranging the loop coils 104 such that they overlap may lead to high mutual coupling between them, particularly if soft magnetic core material is used to boost the $B_1$ field strength of the antenna. If only two sections were required, removing coupling could be accomplished by providing an amount of overlap that minimized such coupling. However, herein, one embodiment includes at least three loop coils distributed along the length of the magnet. With reference now to FIG. 11B, such a configuration could lead to coupling between the first and third 1102, 1106 coils even if the first and second 1102, 1104 coils are arranged to reduce coupling.

Figure 11A:
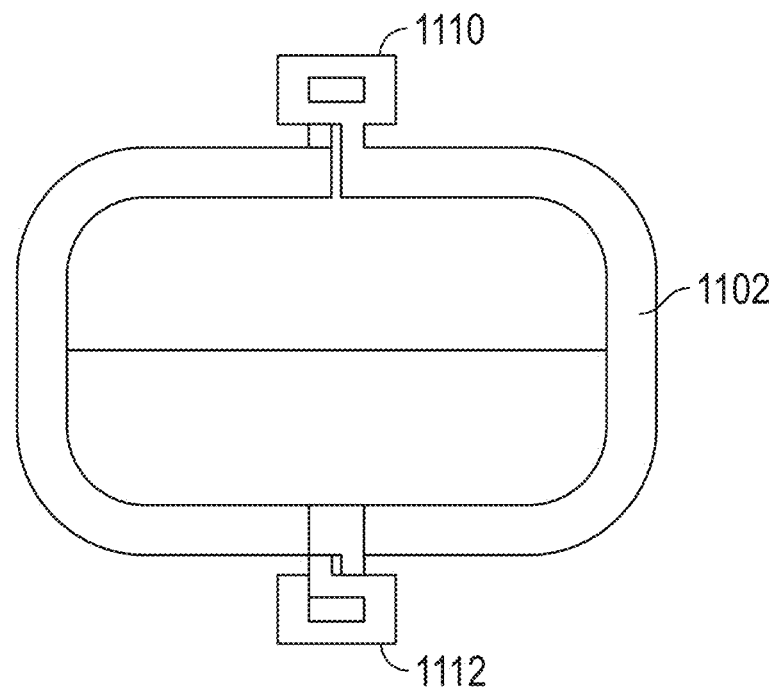
FIGS. 11A-11B show, respectively, a loop coil having additional outer sub-loops and how such loop coils may be overlaid in one embodiment to reduce mutual inductive coupling among more than one receive antenna simultaneously.
Figure 11B:
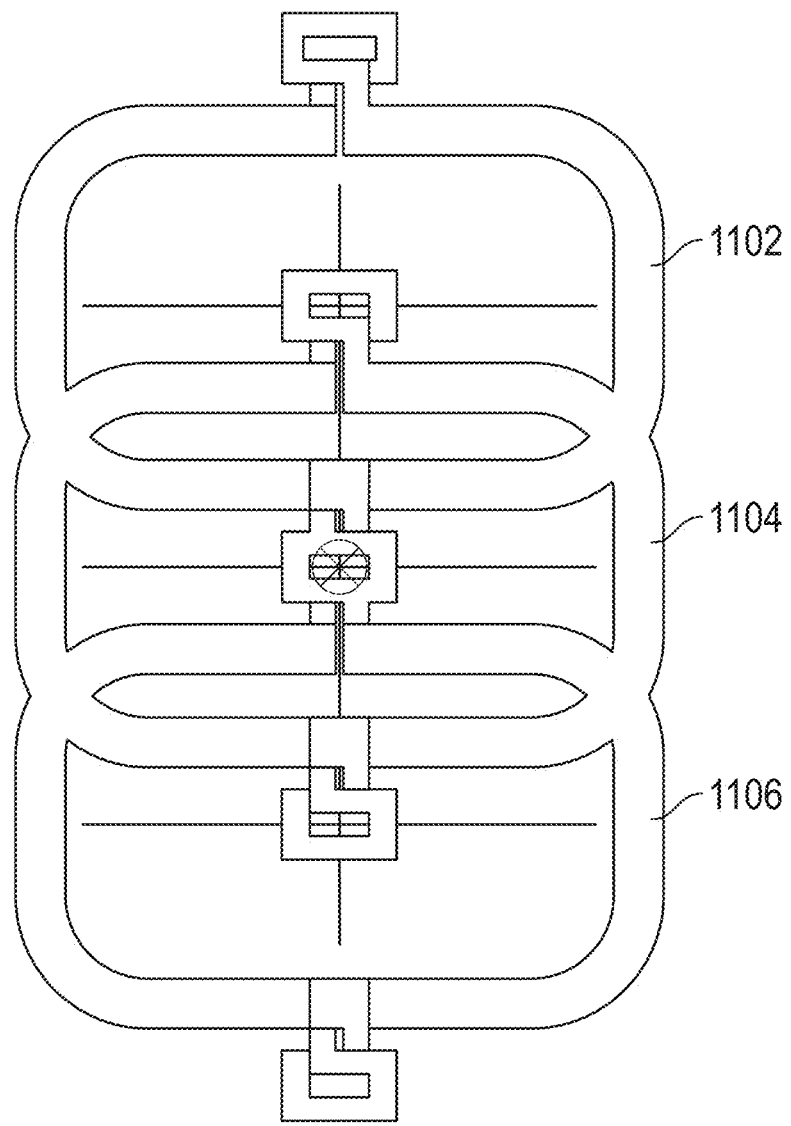

In one embodiment, each coil loop includes small outer loops 1110 and 1112 as shown in FIG. 11A. These outer loops are contiguous with the main coil in one embodiment. The outer loop of nearest non-adjacent neighbor coils (e.g., 1102 and 1106) are overlapped to minimize coupling between them. The amount of overlap between adjacent coils can be determined either empirically or via simulation and is based on loop sizing.

Figure 10:
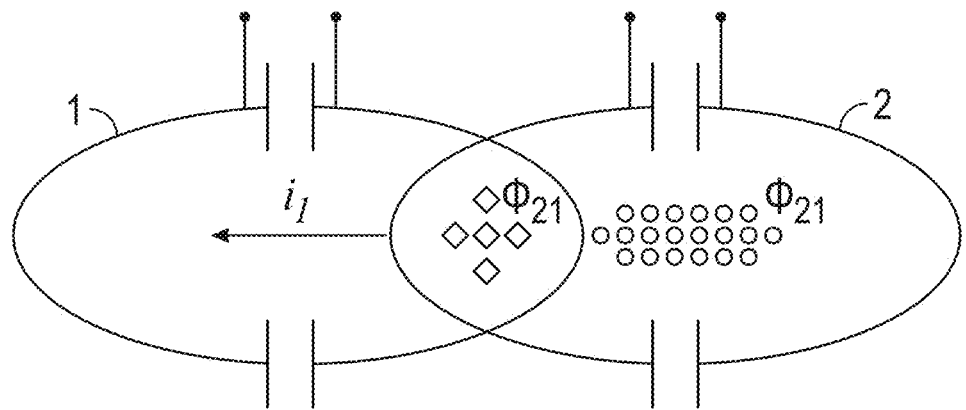
FIG. 10 shown an example arrangement of loop coils to reduce mutual coupling between adjacent antennas of an array.

In particular, and with reference to FIG. 10, a first method for coil decoupling involves eliminating or minimizing the mutual inductance between coils (i.e. make M21=0). One method to do this is to increase the physical distance between coils until the mutual inductance is negligible. Unfortunately, this implies severe restrictions on the coil array geometry, which is ideally optimized based on maximizing the sensitivity of formation measurements. Overlap decoupling is a special case for reducing mutual inductance. As shown in FIG. 10, a pair of coils can be optimally placed such that the primary coil's 1 flux (e.g., $\Phi_{21}$) into and out of a secondary coil 2 is precisely equal and cancels. A benefit of overlap decoupling is that neighboring coils can be closely positioned such that the secondary coil is highly sensitive to the formation predominantly covered by the primary coil, and since measurements are independent, combined signals can result in measurements with higher signal-to-noise ratios over an extended range. The flexibility of multi-channel acquisitions also permits potential gains in logging speed and higher vertical resolution.

Magnetic resonance measurement apparatuses may include an array of receive antenna assemblies distributed about the tool circumference. Each antenna assembly may measure fields so that a larger volume of interest can be interrogated.

Embodiment 1: A nuclear magnetic resonance apparatus for estimating properties of an earth formation, the apparatus comprising: a carrier configured to be deployed in a borehole in the earth formation; at least one transmitting assembly disposed in the carrier and configured to generate an oscillating magnetic field in a volume of interest within the earth formation; at least one receiving assembly disposed in the carrier and configured to detect a nuclear magnetic resonance (NMR) signal originating in the volume of interest; wherein the receiving assembly includes at least a first longitudinal region with a loop coil and a butterfly coil , the loop coil central axis being located over a region of the magnet assembly where a static magnetic field is predominantly along the azimuthal direction to the carrier and the butterfly coil being at least partially overlapped with the loop coil to reduce mutual coupling.

Embodiment 2: The apparatus of any prior embodiment, wherein the butterfly coil is offset angularly/azimuthally about the magnet assembly such that its cross-member resides predominantly at a point of exiting or return static magnetic fields of the carrier .

Embodiment 3: The apparatus of any prior embodiment, wherein the butterfly coil shares a central axis with the loop coil and the butterfly coil cross-member resides in a plane that is transverse to the tool and substantially perpendicular to the longitudinal axis.

Embodiment 4: The apparatus of any prior embodiment, wherein the first longitudinal region includes a second butterfly coil, comprised of two loops and a cross-member, which is located distinctly from the first butterfly coil, and whose cross member resides predominantly at a point of exiting or returning static magnetic field to the magnet assembly.

Embodiment 5: The apparatus of any prior embodiment, wherein the first region includes a third butterfly coil, comprised of two loops and a cross-member, that shares a central axis with the loop coil, wherein the cross-member of the third butterfly coil is substantially perpendicular to the cross-members of the first and second butterfly coils.

Embodiment 6: The apparatus of any prior embodiment, wherein the receiving assembly includes a second longitudinal region including a loop coil and a butterfly coil, comprised of two loops and a cross-member, the loop coil being located at predominantly the same azimuthal rotation angle about the carrier as the loop coil from the first longitudinal region and the butterfly coil being at least partially overlapping with the loop coil at the second longitudinal region.

Embodiment 7: The apparatus of any prior embodiment, wherein the loop coil of the first region and the loop coil of the second region each include an additional outer loop.

Embodiment 8: The apparatus of any prior embodiment, wherein the receiving assembly includes a third longitudinal region having a loop coil and a butterfly coil, comprised of two loops and a cross-member.

Embodiment 9: The apparatus of any prior embodiment, wherein the loop coil of the first region and the loop coil of the third region each include an outer loop.

Embodiment 10: The apparatus of any prior embodiment, wherein the outer loop of the loop coil of the first region and the outer loop of the loop coil of the third region overlap.

Embodiment 11: The apparatus of any prior embodiment, wherein the magnet assembly has a rotating pattern of magnetic fields in a predominantly transverse plane that is perpendicular to a longitudinal axis of the magnet assembly.

Embodiment 12: The apparatus of any prior embodiment, wherein the magnet assembly is a cylindrical or semi-cylindrical structure, and the magnet components comprise a linear array of the longitudinally elongated magnets forming the structure.

Embodiment 13: The apparatus of any prior embodiment, wherein the first longitudinal region contains a second loop coil that is located distinctly from the first loop coil, and whose central axis is located over a region of the magnet assembly where a static magnetic field is predominantly along the azimuthal direction to the carrier.

Embodiment 14: The apparatus of any prior embodiment, further comprising a second butterfly coil comprised of two loops and a cross-member that shares a central axis with the first butterfly coil, and whose cross-member is predominantly perpendicular to the cross-members of the first butterfly coil.

Embodiment 15: The apparatus of any prior embodiment, wherein the first longitudinal region includes first and second butterfly coils sharing a central axis, the first butterfly coil having a cross member predominantly contained in a plane transverse to a longitudinal axis of the carrier, the second butterfly coil having a cross member that is substantially perpendicular to cross member of the first butterfly coil.

Embodiment 16: A nuclear magnetic resonance apparatus for estimating properties of an earth formation, the apparatus comprising: a carrier configured to be deployed in a borehole in the earth formation; at least one transmitting assembly disposed in the carrier and configured to generate an oscillating magnetic field in a volume of interest within the earth formation; at least one receiving assembly disposed in the carrier and configured to detect a nuclear magnetic resonance (NMR) signal originating in the volume of interest; wherein the receiving assembly includes at least a first region, a second region and a third region, each region offset longitudinally along the logging apparatus and including a loop coil having an additional outer loop; wherein the additional outer loop of the loop coil of the first region overlaps the additional outer loop of the loop coil of the third region.

Embodiment 17: The apparatus of any prior embodiment, wherein the loop coil of the first region overlaps the loop coil of the second region.

Embodiment 18: The apparatus of any prior embodiment, wherein the loop coil of the second region overlaps loop coil of the third region.

Embodiment 19: The apparatus of any prior embodiment, wherein the first region includes a first butterfly coil, comprised of two loops and a cross-member, and the cross-member is located where the $B_0$ field is entering or exiting the carrier at a maximum or near maximum value.

Embodiment 20: The apparatus of any prior embodiment, wherein the first region includes a second butterfly coil having two loops and a cross-member.

Embodiment 21: The apparatus of any prior embodiment, wherein the first region includes a third butterfly coil, having two loops and a cross-member, and the cross-member of the third butterfly coil is substantially perpendicular to the cross-members of the first and second butterfly coils.

Embodiment 22: The apparatus of any prior embodiment, wherein the array of longitudinally elongated magnets has a rotating pattern of magnetic orientations in a transverse plane predominantly perpendicular to a longitudinal axis of the magnet assembly.

Embodiment 23: The apparatus of any prior embodiment, wherein the first region includes a first butterfly coil, comprised of two loops and a cross-member, whose central axis is shared with the loop coil.

In connection with the teachings herein, various analyses and/or analytical components may be used, including digital and/or analog subsystems. The system may have components such as a processor, storage media, memory, input, output, communications link (wired, wireless, pulsed mud, optical or other), user interfaces, software programs, signal processors and other such components (such as resistors, capacitors, inductors, etc.) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user, or other such personnel, in addition to the functions described in this disclosure.

One skilled in the art will recognize that the various components or technologies may provide certain necessary or beneficial functionality or features. Accordingly, these functions and features may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

What is claimed is:

1. A nuclear magnetic resonance apparatus for estimating properties of an earth formation, the apparatus comprising:
a carrier configured to be deployed in a borehole in the earth formation;
at least one magnet assembly disposed in the carrier to generate a statis magnetic field within a volume of interest within the earth formation;
at least one transmitting assembly disposed in the carrier and configured to generate an oscillating magnetic field in the volume of interest within the earth formation; and
at least one receiving assembly disposed in the carrier and configured to detect a nuclear magnetic resonance (NMR) signal originating in the volume of interest;
wherein the receiving assembly includes at least a first longitudinal region with a loop coil and a butterfly coil, the loop coil central axis being located over a region of the magnet assembly where a static magnetic field is predominantly along an azimuthal direction to the carrier and the butterfly coil being at least partially overlapped with the loop coil to reduce mutual coupling.

2. The apparatus of claim 1, wherein the butterfly coil is offset angularly/azimuthally about the magnet assembly such that its cross-member resides predominantly at a point of exiting or return static magnetic fields of the carrier.

3. The apparatus of claim 1, wherein the butterfly coil shares a central axis with the loop coil and the cross-member of the butterfly coil resides in a plane that is substantially transverse to the carrier and perpendicular to a longitudinal axis of the carrier.

4. The apparatus of claim 1, wherein the first longitudinal region includes a second butterfly coil, comprised of two loops and a cross-member, which is located distinctly from the first butterfly coil, and whose cross member resides predominantly at a point of exiting or returning static magnetic field to the magnet assembly.

5. The apparatus of claim 4, wherein the first longitudinal region includes a third butterfly coil, comprised of two loops and a cross-member, that shares a central axis with the loop coil, wherein the cross-member of the third butterfly coil is substantially perpendicular to the cross-members of the first and second butterfly coils.

6. The apparatus of claim 1, wherein the receiving assembly includes a second longitudinal region including a loop coil and a butterfly coil, comprised of two loops and a cross-member, the loop coil in the second longitudinal region being located at the same azimuthal rotation angle about the carrier as the loop coil from the first longitudinal region and the butterfly coil being at least partially overlapping with the loop coil at the second longitudinal region.

7. The apparatus of claim 6, wherein the loop coil of the first region and the loop coil of the second region each include an additional outer loop.

8. The apparatus of claim 6, wherein the receiving assembly includes a third longitudinal region having a loop coil and a butterfly coil, comprised of two loops and a cross-member.

9. The apparatus of claim 8, wherein the loop coil of the first region and the loop coil of the third region each include an outer loop.

10. The apparatus of claim 9, wherein the outer loop of the loop coil of the first region and the outer loop of the loop coil of the third region overlap.

11. The apparatus of claim 1, wherein the magnet assembly has a rotating pattern of magnetic fields in a transverse plane that is perpendicular to a longitudinal axis of the magnet assembly.

12. The apparatus of claim 1, wherein the magnet assembly is a cylindrical or semi-cylindrical structure, and its magnet components comprise a linear array of longitudinally elongated magnets.

13. The apparatus of claim 1, wherein the first longitudinal region contains a second loop coil that is located distinctly from the loop coil, and whose central axis is located over a region of the magnet assembly where a static magnetic field is predominantly along the azimuthal direction to the carrier.

14. The apparatus of claim 13, further comprising a second butterfly coil comprised of two loops and a cross-member that shares a central axis with the butterfly coil, and whose cross-member is substantially perpendicular to the cross-member of the butterfly coil.

15. The apparatus of claim 1, wherein the first longitudinal region includes a second butterfly coils sharing a central axis with the butterfly coil, the cross member of the butterfly coil being contained in a plane transverse to a longitudinal axis of the carrier, the second butterfly coil having a cross member that is predominantly perpendicular to the cross member of the butterfly coil.

16. A nuclear magnetic resonance apparatus for estimating properties of an earth formation, the apparatus comprising:
  a carrier configured to be deployed in a borehole in the earth formation;
  at least one transmitting assembly disposed in the carrier and configured to generate an oscillating magnetic field in a volume of interest within the earth formation; and
  at least one receiving assembly disposed in the carrier and configured to detect a nuclear magnetic resonance (NMR) signal originating in the volume of interest;
  wherein the receiving assembly includes at least a first region, a second region and a third region, each region offset longitudinally along the carrier and including a loop coil having an additional outer loop;
  wherein the additional outer loop of the loop coil of the first region overlaps the additional outer loop of the loop coil of the third region.

17. The apparatus of claim 16, wherein the loop coil of the first region overlaps the loop coil of the second region.

18. The apparatus of claim 17, wherein the loop coil of the second region overlaps loop coil of the third region.

19. The apparatus of claim 16, wherein the first region includes a first butterfly coil, comprised of two loops and a cross-member, and the cross-member is located where a $B_0$ field is entering or exiting the carrier at a maximum value.

20. The apparatus of claim 19, wherein the first region includes a second butterfly coil having two loops and a cross-member.

21. The apparatus of claim 20, wherein the first region includes a third butterfly coil, having two loops and a cross-member, and the cross-member of the third butterfly coil is substantially perpendicular to the cross-members of the first and second butterfly coils.

22. The apparatus of claim 16, wherein the transmitting assembly includes a magnet assembly with an array of longitudinally elongated magnets that have a rotating pattern of magnetic orientations in a transverse plane predominantly perpendicular to a longitudinal axis of the magnet assembly.

23. The apparatus of claim 16, wherein the first region includes a first butterfly coil, comprised of two loops and a cross-member, whose central axis is shared with a central axis of the loop coil in the first region.

* * * * *